United States Patent
Gore et al.

(10) Patent No.: US 9,579,385 B2
(45) Date of Patent: Feb. 28, 2017

(54) OPHTHALMIC COMPOSITIONS COMPRISING POLYVINYL CAPROLACTAM-POLYVINYL ACETATE-POLYETHYLENE GLYCOL GRAFT COPOLYMERS

(71) Applicant: Allergan, Inc., Irvine, CA (US)

(72) Inventors: Anuradha V. Gore, Aliso Viejo, CA (US); Chetan P. Pujara, Irvine, CA (US); Richard S. Graham, Irvine, CA (US); Melissa Gulmezian, Irvine, CA (US); Kristin Prinn, Costa Mesa, CA (US); Ramakrishnan Srikumar, Aliso Viejo, CA (US)

(73) Assignee: ALLERGAN, INC., Irvine, CA (US)

(*) Notice: Subject to any disclaimer, the term of this patent is extended or adjusted under 35 U.S.C. 154(b) by 0 days.

(21) Appl. No.: 14/152,380

(22) Filed: Jan. 10, 2014

(65) Prior Publication Data

US 2014/0128329 A1 May 8, 2014

Related U.S. Application Data

(63) Continuation of application No. 13/715,972, filed on Dec. 14, 2012, now abandoned.

(60) Provisional application No. 61/576,453, filed on Dec. 16, 2011.

(51) Int. Cl.

| | | |
|---|---|---|
| *A61K 38/00* | (2006.01) |
| *A61K 47/32* | (2006.01) |
| *A61K 9/00* | (2006.01) |
| *A61K 9/08* | (2006.01) |
| *A61K 31/498* | (2006.01) |
| *A61K 31/5575* | (2006.01) |
| *A61K 31/407* | (2006.01) |
| *A61K 31/417* | (2006.01) |
| *A61K 31/4178* | (2006.01) |
| *A61K 31/496* | (2006.01) |
| *A61K 31/4985* | (2006.01) |
| *A61K 31/5377* | (2006.01) |
| *A61K 31/568* | (2006.01) |
| *A61K 31/573* | (2006.01) |
| *A61K 38/13* | (2006.01) |
| *A61K 47/02* | (2006.01) |
| *A61K 47/18* | (2006.01) |

(52) U.S. Cl.
CPC ............ *A61K 47/32* (2013.01); *A61K 9/0048* (2013.01); *A61K 9/08* (2013.01); *A61K 31/407* (2013.01); *A61K 31/417* (2013.01); *A61K 31/4178* (2013.01); *A61K 31/496* (2013.01); *A61K 31/498* (2013.01); *A61K 31/4985* (2013.01); *A61K 31/5377* (2013.01); *A61K 31/5575* (2013.01); *A61K 31/568* (2013.01); *A61K 31/573* (2013.01); *A61K 38/13* (2013.01); *A61K 47/02* (2013.01); *A61K 47/186* (2013.01)

(58) Field of Classification Search
None
See application file for complete search history.

(56) References Cited

U.S. PATENT DOCUMENTS

| 2003/0199507 | A1 | 10/2003 | Chang | |
|---|---|---|---|---|
| 2005/0276867 | A1 | 12/2005 | Lyons | |
| 2006/0122277 | A1* | 6/2006 | Wong | 514/567 |
| 2008/0146497 | A1* | 6/2008 | Graham et al. | 514/11 |
| 2010/0150992 | A1 | 6/2010 | Kawahara | |
| 2013/0023536 | A1* | 1/2013 | Graham et al. | 514/249 |

FOREIGN PATENT DOCUMENTS

| WO | 2010-102078 | 9/2010 |
|---|---|---|
| WO | 2013-013143 | 1/2013 |

OTHER PUBLICATIONS

Ishikawa et al, Antibacterial activity of surfactants against *Escherichia coli* cells is influenced by carbon source and anaerobiosis, Journal of Applied Microbiology 2002, 93, 302-309.*
Saettone, Progress and Problems in Ophthalmic Drug Delivery, Business Briefing: Pharmatech 2002.*
Reintjes, Solubility Enhancement with BASF Pharma Polymers, Oct. 2011.*
Hughey et al, Thermal processing of a poorly water-soluble drug substance exhibiting a high melting point: The utility of KinetiSol® Dispersing, International Journal of Pharmaceutics 419 (2011) 222-230.*
BASF (News Release, Oct. 6, 2010).*
BASF, The Chemical Company, Soluplus-Technical Information, Soluplus-Technical Information, Jul. 2010, 8 pages, n/a, BASF SE.
Netland, Peter et al, Brimonidine Purite and Brimatoprost Compared With Timolol and Latanoprost in Patients With Glaucoma and Ocular Hypertension, Advances in Therapy, 2003, 20-30, 20 (1).
Yashchuk, Sofiya et al, Assessment of Cellular Irritation Potential os Soluplus&[reg]—A Novel, Mild, and Versatile Excipient, AAPS, 2012, 2 pages.
International Searching Authority, Notification of Transmittal of the International Search Report and the Written Opinion of the International Searching Authority, Aug. 9, 2013.

* cited by examiner

*Primary Examiner* — James H Alstrum Acevedo
*Assistant Examiner* — Sergio Coffa
(74) *Attorney, Agent, or Firm* — Lorenz Siddiqi

(57) ABSTRACT

Compositions and methods related to ophthalmic use of polyvinyl caprolactam-polyvinyl acetate-polyethylene glycol graft copolymers and therapeutic uses are described herein.

37 Claims, No Drawings

OPHTHALMIC COMPOSITIONS COMPRISING POLYVINYL CAPROLACTAM-POLYVINYL ACETATE-POLYETHYLENE GLYCOL GRAFT COPOLYMERS

RELATED APPLICATION

This application is a continuation of U.S. patent application Ser. No. 13/715,972, filed Dec. 14, 2012, which claims the benefit of U.S. Provisional Application Ser. No. 61/576,453, filed Dec. 16, 2011, both of which are incorporated herein by reference in their entirety.

BACKGROUND

Topically applied formulations, such as those applied to the cornea, conjunctiva, eyelid margin, etc., are frequently used in ophthalmology to treat acute and chronic conditions because they may be safer than systemically delivered formulations. However, some therapeutically active agents may have poor solubility in aqueous solutions, which may limit topical ophthalmic use. Solubility may be improved for some therapeutically active agents by using a nonionic surfactant, but further improvement may be needed.

SUMMARY

Some embodiments include a topical ophthalmic composition comprising a polyvinyl caprolactam-polyvinyl acetate-polyethylene glycol graft copolymer (PCA-PVA-PEG).

Some embodiments include a method of solubilizing a therapeutically active agent comprising providing a composition including the therapeutically active agent and a PCA-PVA-PEG. In some embodiments, the therapeutically active agent may not be completely soluble in the composition at room temperature without the PCA-PVA-PEG.

Some embodiments include a method of stabilizing a therapeutically active agent comprising combining the therapeutically active agent with a PCA-PVA-PEG to thereby improve stability of the therapeutically active agent.

Some embodiments include a method of solubilizing a therapeutically active agent comprising mixing the therapeutically active agent and a polyvinyl caprolactam-polyvinyl acetate-polyethylene glycol graft copolymer so that a composition described herein is formed.

Some embodiments include a method of stabilizing a therapeutically active agent comprising combining the therapeutically active agent and a polyvinyl caprolactam-polyvinyl acetate-polyethylene glycol graft copolymer so that a composition described herein is formed.

Some embodiments include a method of treating a disease affecting an eye comprising administering a composition described herein to an eye in need thereof.

Other embodiments of the invention include:

1) A topical ophthalmic composition comprising a polyvinyl caprolactam-polyvinyl acetate-polyethylene glycol graft copolymer.
2) The composition of paragraph 1, wherein the polyvinyl caprolactam-polyvinyl acetate-polyethylene glycol graft copolymer has an average molecular weight of about 10,000 g/mol to about 500,000 g/mol.
3) The composition of paragraphs 1 or 2, further comprising a therapeutically active agent.
4) The composition of paragraph 3, wherein the therapeutically active agent comprises an immunosuppressant, an alpha-adrenergic antagonist, a steroid, a prostaglandin EP2 agonist, a muscarinic, a prostaglandin, an alpha agonist, an antibiotic, an anti-infective agent, an anti-inflammatory, a beta blocker, or a combination thereof.
5) The composition of paragraph 3, wherein the therapeutically active agent comprises cyclosporine A, a cyclosporine analog, phentolamine, testosterone, dexamethasone, prednisolone, bimatoprost, latanoprost, Compounds A, B, C, D, E, F, G and H of Table 8, pilocarpine, brimonidine, gatifloxacin, ketorolac, a steroid, timolol, or a combination thereof.
6) The composition of paragraph 5, wherein the composition is a solution.
7) The composition of paragraph 6, further comprising a co-solubilizer.
8) The composition of paragraph 7, wherein the co-solubilizer comprises sorbitan monostearate, a polyoxyethylene-polyoxypropylene block copolymer, polyoxyethyleneglyceroltriricinoleate 35, a cyclodextrin, or a combination thereof.
9) The composition of paragraph 6, further comprising an osmolality agent.
10) The composition of paragraph 9, wherein the osmolality agent comprises propylene glycol, glycerin, mannitol, sodium chloride, or a combination thereof.
11) The composition of paragraph 10, further comprising a buffer.
12) The composition of paragraph 11, wherein the buffer comprises phosphate, phosphate and citrate, trolamine, lactate, borate, borate and citrate, or a combination thereof.
13) The composition of paragraph 10 further comprising a preservative.
14) The composition of paragraph 13, wherein the preservative comprises benzalkonium chloride, a stabilized oxychloro complex, or a combination thereof.
15) A method of solubilizing a therapeutically active agent comprising providing a composition comprising the therapeutically active agent and a polyvinyl caprolactam-polyvinyl acetate-polyethylene glycol graft copolymer, wherein the therapeutically active agent is not completely soluble in the composition at room temperature without the polyvinyl caprolactam-polyvinyl acetate-polyethylene glycol graft copolymer.
16) A method of solubilizing a therapeutically active agent comprising mixing the therapeutically active agent and a polyvinyl caprolactam-polyvinyl acetate-polyethylene glycol graft copolymer so that a composition according to claim 5 is formed.
17) A method of stabilizing a therapeutically active agent comprising combining the therapeutically active agent with a polyvinyl caprolactam-polyvinyl acetate-polyethylene glycol graft copolymer to thereby improve stability of the therapeutically active agent.
18) A method of stabilizing a therapeutically active agent comprising combining the therapeutically active agent and a polyvinyl caprolactam-polyvinyl acetate-polyethylene glycol graft copolymer so that a composition according to claim 5 is formed.
19) A method of treating a disease affecting an eye comprising administering a composition according to paragraph 11 to an eye in need thereof wherein one of the active agents is bimatoprost.

20) The method of paragraph 19 further comprising the active agent brimonidine.

DETAILED DESCRIPTION

Polyoxyethylated surfactants such as polysorbate 80, polysorbate 20, and polyoxyl stearate 40 may suffer from disadvantages such as oxidative degradation of therapeutically active agents in a composition, degradation of the surfactant, reduced preservative effectiveness, and reduced permeability of bioavailability of the therapeutically active agent through biological membranes. Use of a PCA-PVA-PEG may help to reduce or prevent these undesirable results.

A polyvinyl caprolactam-polyvinyl acetate-polyethylene glycol graft copolymer (PCA-PVA-PEG) includes a polymer comprising at least one caprolactam block, at least one polyvinyl acetate block, and at least one polyethylene glycol block, wherein at least one block branches from another of the type of blocks. For example, some PCA-PVA-PEGs may be represented by the structure below.

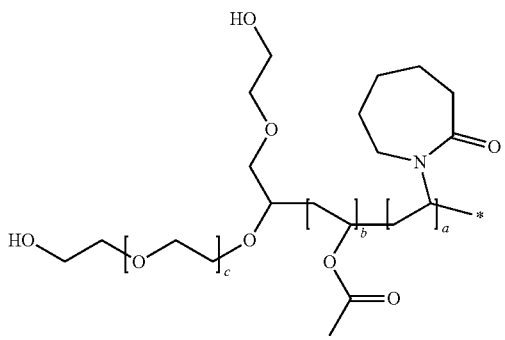

In the structure above, a may be about 10 to about 10,000, about 100 to about 900, about 100 to about 500, or about 500 to about 900.

In the structure above, b may be about 20 to about 20,000, about 150 to about 1500, about 200 to about 800, or about 800 to about 1500.

In the structure above, c may be about 30 to about 30,000, about 300 to about 3000, about 300 to about 1000, about 1000 to about 2000, or about 2000 to about 3000. In some embodiments, a PCA-PVA-PEG may have an average molecular weight of about 1,000 g/mol to about 5,000,000 g/mol, about 10,000 g/mol to about 500,000 g/mol, or about 90,000 g/mol to about 140,000 g/mmol.

In some embodiments, a PCA-PVA-PEG may be a polymer represented by CAS No. 402932-23-4, such as SOLU-PLUS®, available from BASF.

Use of a PCA-PVA-PEG may improve the solubility and/or stability of a therapeutically active agent, including any of those listed below. A PCA-PVA-PEG may also have minimal interference with preservatives, and thus in some compositions may allow less preservative to be used. Furthermore, a PCA-PVA-PEG may have antimicrobial properties in some compositions, and may thus be included in a self-preserved composition that may not need a traditional preservative. A PCA-PVA-PEG may also be synergistic with some preservatives such as stabilized oxychloro complexes.

A therapeutically active agent includes any compound or substance recognized in the official United States Pharmacopoeia, official Homoeopathic Pharmacopoeia of the United States, or official National Formulary, or any supplement to any of them; and any compound or substance intended for use in the diagnosis, cure, mitigation, treatment, or prevention of disease in humans or other animals; and any substance other than food or water intended to affect the structure or any function of the body of humans or other animals.

Some therapeutically active agents may include antihistamines, antibiotics, beta blockers, steroids, antineoplastic agents, immunosuppressive agents, antiviral agents, and mixtures thereof.

Examples of antihistamines may include, but are not limited to, loratadine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimeprazine doxylamine, pheniramine, pyrilamine, chlorcyclizine, thonzylamine, and derivatives thereof.

Examples of antibiotics may include without limitation, cefazolin, cephradine, cefaclor, cephapirin, ceftizoxime, cefoperazone, cefotetan, cefuroxime, cefotaxime, cefadroxil, ceftazidime, cephalexin, cephalothin, cefamandole, cefoxitin, cefonicid, ceforanide, ceftriaxone, cefadroxil, cephradine, cefuroxime, cyclosporine, ampicillin, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, gatifloxacin, ofloxacin, and derivatives thereof.

Examples of beta blockers may include acebutolol, atenolol, labetalol, metoprolol, propranolol, timolol, and derivatives thereof.

Examples of steroids may include corticosteroids, such as cortisone, prednisolone, fluorometholone, dexamethasone, medrysone, loteprednol, deflazacort, hydrocortisone, prednisone, betamethasone, prednisone, methylprednisolone, triamcinolone hexacetonide, paramethasone acetate, diflorasone, fluocinonide, fluocinolone, triamcinolone, derivatives thereof, and mixtures thereof.

Examples of antineoplastic agents may include adriamycin, cyclophosphamide, actinomycin, bleomycin, daunorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, cyclophosphamide, and flutamide, and derivatives thereof.

Examples of immunosuppressive agents may include cyclosporine, azathioprine, tacrolimus, and derivatives thereof.

Examples of antiviral agents may include interferon gamma, zidovudine, amantadine hydrochloride, ribavirin, acyclovir, valacyclovir, dideoxycytidine, phosphonoformic acid, ganciclovir and derivatives thereof.

In some embodiments, a therapeutically active agent may comprise an immunosuppressant, an alpha-adrenergic antagonist, a steroid, a prostaglandin EP2 agonist, a muscarinic, a prostaglandin, an alpha agonist, an antibiotic, an anti-infective agent, an anti-inflammatory, a beta blocker, or a combination thereof. In some embodiments, a therapeutically active agent may comprise cyclosporine A, a cyclosporine analog, phentolamine, testosterone, dexamethasone, prednisolone, bimatoprost, latanoprost, Compounds A, B, C, D, E, F, G and H of Table 8, pilocarpine, brimonidine, gatifloxacin, ketorolac, a steroid, timolol, or a combination thereof.

An ophthalmically acceptable liquid or solution should be tolerable to a patient for topical ophthalmic use. Additionally, an ophthalmically acceptable liquid may be packaged for single use, or contain a preservative to prevent contamination over multiple uses.

For ophthalmic application, solutions or medicaments may be prepared using a physiological saline solution as a major vehicle. Ophthalmic solutions may be maintained at a comfortable pH with an appropriate buffer system. The formulations may also contain conventional, pharmaceutically acceptable preservatives, stabilizers and surfactants.

An ophthalmically acceptable liquid may include a buffer. The buffer may vary, and may include any weak conjugate acid-base pair suitable for maintaining a desirable pH range. Examples include, but are not limited to, acetate buffers, citrate buffers, phosphate buffers, borate buffers, lactate buffers, NaOH/trolamine buffers, or a combination thereof, such as phosphate and citrate or borate and citrate. Acids or bases, such as HCl and NaOH, may be used to adjust the pH of these formulations as needed. The amount of buffer used may vary. In some embodiments, the buffer may have a concentration in a range of about 1 nM to about 100 mM.

An ophthalmically acceptable liquid may include a preservative. The preservative may vary, and may include any compound or substance suitable for reducing or preventing microbial contamination in an ophthalmic liquid subject to multiple uses from the same container. Preservatives that may be used in the pharmaceutical compositions disclosed herein include, but are not limited to, cationic preservatives such as quaternary ammonium compounds including benzalkonium chloride, polyquad, and the like; guanidine-based preservatives including PHMB, chlorhexidine, and the like; chlorobutanol; mercury preservatives such as thimerosal, phenylmercuric acetate and phenylmercuric nitrate; oxidizing preservatives such as stabilized oxychloro complexes (e.g. PURITE®); and other preservatives such as benzyl alcohol. In some embodiments, a preservative may comprise benzalkonium chloride, a stabilized oxychloro complex, or a combination thereof. In some embodiments, a preservative may have a concentration of about 10 ppm to about 200 ppm, about 10 ppm to about 300 ppm, or about 50 ppm to about 150 ppm.

An ophthalmically acceptable liquid may include a co-solubilizer such as a surfactant. The surfactant may vary, and may include any compound that is surface active or can form micelles. A surfactant may be used for assisting in dissolving an excipient or an active agent, dispersing a solid or liquid in a composition, enhancing wetting, modifying drop size, stabilizing an emulsion, or a number of other purposes. Examples of surfactants may include, but are not limited to, surfactants of the following classes: alcohols; amine oxides; block polymers; carboxylated alcohol or alkylphenol ethoxylates; carboxylic acids/fatty acids; ethoxylated alcohols; ethoxylated alkylphenols; ethoxylated aryl phenols; ethoxylated fatty acids; ethoxylated; fatty esters or oils (animal & veg.); fatty esters; fatty acid methyl ester ethoxylates; glycerol esters; glycol esters; lanolin-based derivatives; lecithin and lecithin derivatives; lignin and lignin derivatives; methyl esters; monoglycerides and derivatives; polyethylene glycols; polymeric surfactants; propoxylated & ethoxylated fatty acids, alcohols, or alkyl phenols; protein-based surfactants; sarcosine derivatives; sorbitan derivatives; sucrose and glucose esters and derivatives. In some embodiments, the surfactant may include polyethylene glycol (15)-hydroxystearate (CAS Number 70142-34-6, available as SOLUTOL HS 15® from BASF), a polyoxyethylene-polyoxypropylene block copolymer (CAS No. 9003-11-6, available as PLURONIC® F-68 from BASF), polyoxyethylene 40 stearate (POE40 stearate), polysorbate 80 or polyoxyethylene (80) sorbitan monooleate (CAS No. 9005-65-6), sorbitan monostearate (CAS No. 1338-41-6, available as SPAN™ 60 from Croda International PLC), or polyoxyethyleneglyceroltriricinoleate 35 (CAS No. 61791-12-6, available as CREMOPHOR EL® from BASF), ethoxylated castor oil, such as Cremophor EL (CAS Number 61791-12-6). The amount of surfactant may vary. In some embodiments, the amount of any surfactant such as those listed above may be about 0.001 to about 5%, about 0.1% to about 2%, or about 0.1% to about 1%.

Other compounds, such as a cyclodextrin, may be used as a co-solubilizer. Examples of cyclodextrins may include α-cyclodextrin; β-cyclodextrin; γ-cyclodextrin; cyclodextrin derivatives such as ether and mixed ether derivatives and those derivatives bearing sugar residues such as hydroxyethyl, hydroxypropyl (including 2- and 3-hydroxypropyl) and dihydroxypropyl ethers, their corresponding mixed ethers and further mixed ethers with methyl or ethyl groups, such as methyl-hydroxyethyl, ethyl-hydroxyethyl and ethyl-hydroxypropyl ethers of α-, β- and γ-cyclodextrin; maltosyl, glucosyl and maltotriosyl derivatives of β- and γ-cyclodextrin, which may contain one or more sugar residues, e.g. glucosyl or diglucosyl, maltosyl or dimaltosyl, as well as various mixtures thereof, e.g. a mixture of maltosyl and dimaltosyl derivatives; cyclodextrin derivatives comprising anionic functional groups such as sulfobutylether derivatives, sulfonates, phosphates, and the like, such as hydroxypropyl-β-cyclodextrin, hydroxypropyl-γ-cyclodextrin, sulfobutylether-β-cyclodextrin, and sulfobutylether-γ-cyclodextrin, as well as hydroxyethyl-β-cyclodextrin, hydroxyethyl-γ-cyclodextrin, dihydroxypropyl-β-cyclodextrin, glucosyl-β-cyclodextrin, diglucosyl-β-cyclodextrin, maltosyl-β-cyclodextrin, maltosyl-γ-cyclodextrin, maltotriosyl-β-cyclodextrin, maltotriosyl-γ-cyclodextrin and dimaltosyl-β-cyclodextrin, and mixtures thereof such as maltosyl-β-cyclodextrin/dimaltosyl-β-cyclodextrin. Cyclodextrins may be present at a concentration of about 0.01% to about 30%, about 0.01% to about 10%, or about 1% to about 10%.

In some embodiments, a co-solubilizer may comprise sorbitan monostearate, a polyoxyethylene-polyoxypropylene block copolymer, polyoxyethyleneglyceroltriricinoleate 35, a cyclodextrin, or a combination thereof. An ophthalmically acceptable liquid may include a vehicle. Examples of suitable vehicles include, but are not limited to, polyvinyl alcohol, povidone, hydroxypropyl methyl cellulose, poloxamers, carboxymethyl cellulose, hydroxyethyl cellulose, and acrylates (e.g. PEMULEN®).

An ophthalmically acceptable liquid may include an osmolality agent. The osmolality agent may vary, and may include any compound or substance useful for adjusting the osmolality of an ophthalmic liquid. Examples include, but are not limited to, salts, particularly sodium chloride or potassium chloride, organic compounds such as propylene glycol, mannitol, or glycerin, or any other suitable ophthalmically acceptable osmolality adjustor. In some embodiments, an osmolality agent may comprise propylene glycol, glycerin, mannitol, sodium chloride, or a combination thereof.

The amount of osmolality agent may vary depending upon whether an isotonic, hypertonic, or hypotonic liquid is desired. In some embodiments, the amount of an osmolality agent such as those listed above may be at least about 0.0001% up to about 1%, about 2%, or about 5%.

An ophthalmically acceptable liquid may include an antioxidant. The antioxidant may vary, and may include any compound or substance that is useful in reducing oxidation of any compound present in an ophthalmically acceptable liquid. Examples, but are not limited to, sodium metabisulfite, sodium thiosulfate, acetylcysteine, butylated hydroxyanisole, and butylated hydroxytoluene.

An ophthalmically acceptable liquid may include a chelating agent. The chelating agent may vary, and may include any compound or substance that is capable of chelating a metal. A useful chelating agent is edetate disodium, although other chelating agents may also be used in place or in conjunction with it.

Compositions may be aqueous solutions or emulsions, or some other acceptable liquid form. For an emulsion, one or more oils may be used to form the emulsion. Suitable oils include, but are not limited to anise oil, castor oil, clove oil, cassia oil, cinnamon oil, almond oil, corn oil, arachis oil, cottonseed oil, safflower oil, maize oil, linseed oil, rapeseed oil, soybean oil, olive oil, caraway oil, rosemary oil, peanut oil, peppermint oil, sunflower oil, eucalyptus oil, sesame oil, and the like.

Some ophthalmically acceptable compositions may comprise an ointment or a cream vehicle that may include a polymer thickener, water, preservatives, active surfactants or emulsifiers, antioxidants, and a solvent or mixed solvent system.

Any polymer thickeners suitable for ophthalmic application may be used, such as hydrophilic thickeners frequently used in the pharmaceutical industries. For example, a hydrophilic thickener may comprise an acrylic acid or acrylate polymer, either cross-linked or non cross-linked such as a CARBOPOL® (B.F. Goodrich, Cleveland, Ohio), including CARBOPOL 980®. These polymers may dissolve in water and may form a clear or slightly hazy gel upon neutralization with a base such as sodium hydroxide, potassium hydroxide, triethanolamine, or other amine bases. Other commercially available thickeners may include HYPAN® (Kingston Technologies, Dayton, N.J.), NATROSOL® (Aqualon, Wilmington, Del.), KLUCEL® (Aqualon, Wilmington, Del.), or STABILEZE® (ISP Technologies, Wayne, N.J.). KLUCEL® is a cellulose polymer that may be dispersed in water and may form a uniform gel upon complete hydration. Other useful gelling polymers may include hydroxyethylcellulose, hydroxypropylcellulose, cellulose gum, MVA/MA copolymers, MVE/MA decadiene crosspolymer, PVM/MA copolymer, etc.

Any effective amount of polymer thickener may be used, such as about 0.2% to about 4% weight/weight of the composition. A useful weight/weight percent range for CARBOPOL® may be about 0.1% to about 5%, about 0.1% to about 2%, or about 0.5% to about 2%, a useful weight/weight percent range for NATROSOL® and KLUCEL® may be about 0.5% to about 4%, and a useful weight/weight percent range for HYPAN® or STABILEZE® may be about 0.5% to about 4%.

Preservatives used in an ophthalmic ointment or cream and may comprise about 0.1 to about 10%, about 1% to about 5%, about 0.05% to 0.5%, or about 0.05% to about 0.1% weight/weight of the total composition. The use of preservatives may help to reduce or prevent microorganism growth. Some useful preservatives may include benzyl alcohol, methylparaben, propylparaben, butylparaben, chloroxylenol, sodium benzoate, DMDM Hydantoin, 3-Iodo-2-Propylbutyl carbamate, potassium sorbate, chlorhexidine digluconate, etc.

An ophthalmic composition may be applied in a topical cream. Topical creams may be oil-in-water emulsions or water-in-oil emulsions. An oil phase may include but is not limited to fatty alcohols, acids, or esters such as isopropyl myristate, cetyl palmitate, cetyl alcohol, stearyl alcohol, stearic acid, isopropyl stearate, glycerol stearate, mineral oil, white petrolatum, or other oils alone or in combination. An oil phase may be about 1% to about 50%, about 1% to about 3%, about 10% to about 30%, about 10% to about 25%, about 10% to about 20%, about 20% to about 30%, or about 10% to about 15% weight/weight.

An ophthalmic composition such as those described herein may be useful to treat or prevent ophthalmic diseases or conditions, such as one of the following:

MACULOPATHIES/RETINAL DEGENERATION: Non-exudative age related macular degeneration (ARMD), exudative age related macular degeneration (ARMD), choroidal neovascularization, diabetic retinopathy, acute macular neuroretinopathy, central serous chorioretinopathy, cystoid macular edema, diabetic macular edema.

UVEITIS/RETINITIS/CHOROIDITIS: Acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (MEWDS), ocular sarcoidosis, posterior scleritis, serpiginous choroiditis, subretinal fibrosis and uveitis syndrome, Vogt-Koyanagi-Harada syndrome.

VASCUCLAR DISEASES/EXUDATIVE DISEASES: Retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, Eales disease.

TRAUMATIC/SURGICAL: Sympathetic ophthalmia, uveitic retinal disease, retinal detachment, trauma, laser, PDT, photocoagulation, hypoperfusion during surgery, radiation retinopathy, bone marrow transplant retinopathy.

PROLIFERATIVE DISORDERS: Proliferative vitreal retinopathy and epiretinal membranes, proliferative diabetic retinopathy, retinopathy of prematurity (retrolental fibroplastic).

INFECTIOUS DISORDERS: Ocular histoplasmosis, ocular toxocariasis, presumed ocular histoplasmosis syndrome (POHS), endophthalmitis, toxoplasmosis, retinal diseases associated with HIV infection, choroidal disease associated with HIV infection, uveitic disease associated with HIV infection, viral retinitis, acute retinal necrosis, progressive outer retinal necrosis, fungal retinal diseases, ocular syphilis, ocular tuberculosis, diffuse unilateral subacute neuroretinitis, myiasis.

GENETIC DISORDERS: Retinitis pigmentosa, systemic disorders with associated retinal dystrophies, congenital stationary night blindness, cone dystrophies, fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum, Osler Weber syndrome.

RETINAL TEARS/HOLES: Retinal detachment, macular hole, giant retinal tear.

TUMORS: Retinal disease associated with tumors, solid tumors, tumor metastasis, benign tumors, for example, hemangiomas, neurofibromas, trachomas, and pyogenic granulomas, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors.

MISCELLANEOUS: Punctate inner choroidopathy, acute posterior multifocal placoid pigment epitheliopathy, myopic retinal degeneration, acute retinal pigment epithelitis, ocular inflammatory and immune disorders, ocular vascular malfunctions, corneal graft rejection, neovascular glaucoma and the like.

Example 1

Table 1 summarizes solubility of bimatoprost in vehicles with 5 different solubilizers over a range of temperatures. Solubility of bimatoprost in vehicle containing PCA-PVA-PEG is higher than other solubilizers at room temperature (RT) and elevated temperatures.

TABLE 1

Bimatoprost Solubility in five different formulation vehicles at different temperatures. At room temperature and elevated temperatures, PCA-PVA-PEG shows the highest solubilization for bimatoprost

| Solubilizer used (conc. of solubilizer is 1%) | Temperature (° C.) | Solubility (mg/ml) |
|---|---|---|
| SOLUPLUS ® | 5 | 0.427* |
| (PCA-PVA-PEG) | 25 | 3.513* |
|  | 40 | 4.751* |
| SOLUTOL ® HS 15 | 5 | 1.502** |
|  | 25 | 1.320** |
|  | 40 | 1.237** |
| Polysorbate 20 | 5 | 1.242** |
|  | 25 | 1.178** |
|  | 40 | 1.050** |
| POE 40 Stearate | 5 | 1.268** |
|  | 25 | 1.213** |
|  | 40 | 1.149** |
| Polysorbate 80 | 5 | 1.678** |
|  | 25 | 1.524** |
|  | 40 | 1.457** |

*Measured at 1 week only;
**Measured at 8 weeks

Example 2

Data in Support of Improved BAK Efficacy

Preservative titration studies were performed to compare the efficacy of BAK in formulations using different solubilizers. Typically, it is seen that in the presence of surfactants, the preservative efficacy of BAK is significantly reduced. As a result, higher levels of BAK may be required to meet the preservative criteria for ophthalmic products as defined in USP <51> and European Pharmacopeias 5.1.3 chapters. It was seen that when PCA-PVA-PEG was used as a solubilizer, the preservative criteria were met at lower levels of BAK as compared to all other surfactants tested as summarized in Table 2. In fact, formulations containing PCA-PVA-PEG met PhEurA criteria with as low as 50 ppm BAK, which is similar to formulations containing no solubilizers.

TABLE 2

Summary of Preservative Titration to Failure results for formulations containing different solubilizers.

| | APET Criteria Met[1] | | | | |
|---|---|---|---|---|---|
| BAK (ppm) | 1% SOLUPLUS ® | 1% PS80 F1 Solution Series | 1% SOLUTOL ® F2 Solution Series | 1% PS20 F3 Solution Series | 1% POE40 F4 Solution Series |
| 50 | Ph Eur-A | USP | Ph Eur-B | USP | USP |
| 75 | Not tested | Ph Eur-B | Ph Eur-B | Ph Eur-B | USP |
| 100 | Ph Eur-A | Ph Eur-B | Ph Eur-A | Ph Eur-B | Ph Eur-B |
| 120 | Ph Eur-A | Ph Eur-B | Ph Eur-A | Ph Eur-B | Ph Eur-B |
| 140 | Ph Eur-A | Ph Eur-A | Ph Eur-A | Ph Eur-A | Ph Eur-B |
| 160 | Ph Eur-A | Ph Eur-A | Ph Eur-A | Ph Eur-A | Ph Eur-B |
| Expt # | 22955 | 22358 | 22839 | 22861 | 22861 |

[1]APET criteria as defined in USP <51> and European Pharmacopeia (Ph Eur) 5.1.3.

Example 3

Use of PCA-PVA-PEG in a Self-Preserved System

Formulations containing PCA-PVA-PEG demonstrate antimicrobial activity even without use of any preservative. Formulations evaluated are listed in Table 3 along with the APET testing results. It was found that formulations containing 1% PCA-PVA-PEG and phosphate-citrate buffer (formulation 1) met USP criteria for all organisms. Replacing phosphate buffer with borate buffer and removing EDTA allows the formulations to meet PhEurB criteria for all organisms at PCA-PVA-PEG concentrations of 0.5%-1% (formulations 3-5).

TABLE 3

Effect of PCA-PVA-PEG Level and Boric Acid Buffer in APET testing

| | Concentration (% w/v) | | | | | | |
|---|---|---|---|---|---|---|---|
| Formulation | 1 | 2 | 3 | 4 | 5 | 6 | 7 |
| SOLUPLUS ® (PCA-PVA-PEG) | 1.0 | 1.0 | 1.0 | 0.75 | 0.5 | 0.25 | 0.1 |
| Edetate Disodium | 0.01 | 0.01 | 0 | 0 | 0 | 0 | 0 |
| Boric Acid | 0 | 0.6 | 0.6 | 0.6 | 0.6 | 0.6 | 0.6 |
| Sodium Phosphate Dibasic Heptahydrate | 0.268 | 0 | 0 | 0 | 0 | 0 | 0 |
| Citric Acid Monohydrate | 0.014 | 0 | 0 | 0 | 0 | 0 | 0 |
| Glycerin | 1.2 | 1.2 | 1.2 | 1.2 | 1.2 | 1.2 | 1.2 |
| Mannitol | 2.0 | 0 | 0 | 0 | 0 | 0 | 0 |
| 1N NaOH/1N HCl | 7.4 | 7.4 | 7.4 | 7.4 | 7.4 | 7.4 | 7.4 |
| Purified Water | QS | QS | QS | QS | QS | QS | QS |
| APET results (Expt #22994) | | | | | | | |
| PhEurA | Fail | Fail | Fail | Fail | Fail | Fail | Fail |
| PhEurB | Fail | Fail | Pass | Pass | Pass | Fail | Fail |
| USP | Pass | Pass | Pass | Pass | Pass | Pass | Pass |

Example 4

Synergistic Effect of PCA-PVA-PEG on Antimicrobial Efficacy of Purite as Preservative Purite preserved formulations typically meet PhEurB criteria for APET due to lack of sufficient kill for bacteria at the 6 hour time point and mold at the 7 day time point. Combination of Purite with PCA-PVA-PEG (SOLUPLUS®), it was seen that these formulations meet PhEurA criteria (Table 4). It was observed that a combination of 0.5% SOLUPLUS® with 100 ppm Purite was sufficient to meet PhEurA criteria for APET (Table 5). More importantly, excellent log-kill ratios were observed for all organisms tested at the 6 hour time point (for bacteria) and 7 day time point (for fungi).

The combination of Purite, Boric acid and PCA-PVA-PEG would be of utility in over-the-counter (OTC) products. Addition of 0.5% PCA-PVA-PEG in Allergan products such as REFRESH®, REFRESH PLUS®, REFRESH DRY EYE®, OPTIVE® and Next Generation Emulsion would allow these products to meet PhEurA criteria for APET testing. Similarly, for drug products such as ALPHAGAN P®, addition of PCA-PVA-PEG and meeting PhEurA criteria would make this product suitable for filing in the EU.

TABLE 4

Effect of PCA-PVA-PEG and boric acid in combination with Purite on APET

| | Concentration (% w/v) | | | | | |
|---|---|---|---|---|---|---|
| Formulation | Control | 1 | 2 | 3 | 4 | 5 |
| SOLUPLUS ® ® (Polyvinyl caprolactam - polyvinyl acetate- polyethylene glycol graft copolymer) | 1.0 | 1.0 | 1.0 | 1.0 | 1.0 | 1.0 |
| Purite | 0 | 0.002 | 0.004 | 0.006 | 0.008 | 0.010 |
| Boric Acid | 0.6 | 0.6 | 0.6 | 0.6 | 0.6 | 0.6 |
| Glycerin | 1.2 | 1.2 | 1.2 | 1.2 | 1.2 | 1.2 |
| 1N NaOH/1N HCl | 7.4 | 7.4 | 7.4 | 7.4 | 7.4 | 7.4 |
| Purified Water | QS | QS | QS | QS | QS | QS |

TABLE 4-continued

Effect of PCA-PVA-PEG and boric acid in combination with Purite on APET

| | Concentration (% w/v) | | | | | |
|---|---|---|---|---|---|---|
| Formulation | Control | 1 | 2 | 3 | 4 | 5 |
| APET results (Expt #22994) | | | | | | |
| PhEurA | Fail | Pass | Pass | Pass | Pass | Pass |
| PhEurB | Pass | Pass | Pass | Pass | Pass | Pass |
| USP | Pass | Pass | Pass | Pass | Pass | Pass |

TABLE 5

Effect of different levels of PCA-PVA-PEG with Purite on APET

| | Concentration (% w/v) | | | | | |
|---|---|---|---|---|---|---|
| Formulation | 1 | 2 | 3 | 4 | 5 | 6 |
| SOLUPLUS ® ® (Polyvinyl caprolactam - polyvinyl acetate- polyethylene glycol graft copolymer) | 1.0 | 0.75 | 0.5 | 0.25 | 0.1 | 0 |
| Purite | 0.01 | 0.01 | 0.01 | 0.01 | 0.01 | 0.01 |
| Boric Acid | 0.6 | 0.6 | 0.6 | 0.6 | 0.6 | 0.6 |
| Glycerin | 1.5 | 1.5 | 1.5 | 1.5 | 1.5 | 1.5 |
| 1N NaOH/1N HCl | 7.4 | 7.4 | 7.4 | 7.4 | 7.4 | 7.4 |
| Purified Water | QS | QS | QS | QS | QS | QS |
| APET 14 day results (Expt #23017) | | | | | | |
| PhEurA | Pass | Pass | Pass | Fail | Fail | Fail |
| PhEurB | Pass | Pass | Pass | Pass | Pass | Pass |
| USP | Pass | Pass | Pass | Pass | Pass | Pass |

Example 5

Cytotoxicity Testing of PCA-PVA-PEG Formulations

Formulations containing PCA-PVA-PEG ranging from a concentration of 0.25% to 2% were evaluated in Human Corneal Epithelial Cells in-vitro. The cells were incubated with the formulations for 16 hours at 37° C. and the cell viability was measured. It was found that all the PCA-PVA-PEG formulations were non-cytotoxic. Viability of cells treated with PCA-PVA-PEG containing formulations was comparable to those without PCA-PVA-PEG or with Polysorbate 80.

TABLE 6

Cytotoxicity testing of Formulations containing PCA-PVA-PEG

| Formulation | Concentration (% w/v) | | | | | | |
|---|---|---|---|---|---|---|---|
| | 1 | 2 | 3 | 4 | 5 | 6 | 7 |
| Solubilizer: SOLUPLUS ® Polyvinyl caprolactam - polyvinyl acetate- polyethylene glycol graft copolymer | 1.0 | 0.75 | 0.5 | 0.25 | 0.1 | 0.0 | 0.0 |
| Polysorbate 80 | 0.0 | 0.0 | 0.0 | 0.0 | 0.0 | 0.0 | 1.0 |
| Boric Acid | 0.6 | 0.6 | 0.6 | 0.6 | 0.6 | 0.6 | 0.6 |
| Glycerin | 1.5 | 1.5 | 1.5 | 1.5 | 1.5 | 1.5 | 1.5 |
| Mannitol | 0 | 0 | 0 | 0 | 0 | 0 | 0 |
| 1N NaOH/1N HCl | 7.4 | 7.4 | 7.4 | 7.4 | 7.4 | 7.4 | 7.4 |
| Purified Water | QS | QS | QS | QS | QS | QS | QS |
| Results for in-vitro cytotoxicity | | | | | | | |
| % Viability compared to normal saline | 84 ± 3 | 83 ± 3 | 92 ± 3 | 89 ± 6 | 90 ± 2 | 92 ± 1 | 90 ± 4 |

Example 6

Data Showing Improved Stability of Drug Substances in Formulations Containing PCA-PVA-PEG Stability of cyclosporine analogs was evaluated in formulations using Polysorbate 80 (PS80) or PCA-PVA-PEG as solubilizer. Improved stability of the compounds was observed when either PCA-PVA-PEG or SOLUTOL® was used as the solubilizer. An example for Compound H is shown in Table 8. The formulations were prepared in a vehicle containing a citrate-phosphate buffer at pH 7.2 and using PS80, SOLUTOL® or PCA-PVA-PEG at 1% concentration as the solubilizer. Samples were stored at 40° C. conditions and analyzed after 4 weeks. With either SOLUTOL® or PCA-PVA-PEG, the recovery of the drug was two-fold higher than that compared with PS80. Compound H is susceptible to degradation by oxidation. It is believed that both SOLUTOL® and PCA-PVA-PEG may improve stability for these types of compounds by reducing oxidation.

TABLE 7

Stability of Compound H at 0.01% in MP500 bottles at 40° C.

| Vehicle | % Recovery at 4-weeks at 40° C. |
|---|---|
| 1% PS80 | 33.9 |
| 1% SOLUTOL ® | 72.3 |
| 1% SOLUPLUS ® | 69.6 |

Other components of the vehicle: citrate/phosphate buffer and NaCl at pH ~7.2

Example 7

Examples of Classes of APIs and Formulations that May be Formulated with PCA-PVA-PEG for Ophthalmic Use PCA-PVA-PEG may be used as a solubilizer or an additive to formulations with a large variety of actives. These include, but are not limited to, examples listed in Table 8. Table 9 lists examples of solution formulations that may be prepared with PCA-PVA-PEG. It may be used in formulations other than aqueous solution as well. These include, but are not limited to, examples listed in Table 10.

TABLE 8

Examples of APIs that may be formulated using PCA-PVA-PEG

| Drug class | Examples | Typical concentration range in Ophthalmic products |
|---|---|---|
| Immunosuppressant | Cyclosporine A, Cyclosporine analogs | 0.001-0.4% |
| Alpha-adrenergic antagonist | Phentolamine | 0.001-2% |
| Steroids | Testosterone, Dexamethasone, Prednisolone | 0.001-5% |
| EP-2 agonists | Compound A (below) | 0.001-0.1% |
| | Compound B (below) | 0.0002-0.05% |
| | Compound E (below) | 0.001-0.1% |
| Muscarinics | Pilocarpine | 0.1-6.0% |
| Prostaglandins | Bimatoprost, Latanoprost | 0.001-0.1 |
| Alpha-agonists | Brimonidine, Compounds C, D, E and F (below) | 0.001-1% |
| Antibiotics/anti-infectives | Gatifloxicin | 0.1-1% |
| Anti-inflammatory | Ketorolac Steroids | 0.01-1% |

TABLE 8-continued

Examples of APIs that may be formulated using PCA-PVA-PEG

| Drug class | Examples | Typical concentration range in Ophthalmic products |
|---|---|---|
| Beta Blockers | Timolol | 0.05-0.5% |
| Compound A | [structure] | IUPAC Name: isopropyl 5-((((R)-1-(4-((S)-1-hydroxyhexyl)phenyl)-5-oxopyrrolidin-2-yl)methoxy)methyl)-thiophene-2-carboxylate |
| Compound B | [structure] | IUPAC Name: isopropyl 5-(3-((S)-1-(4-((S)-1-hydroxyhexyl)phenyl)-5-oxopyrrolidin-2-yl)propyl)thiophene-2-carboxylate |
| Compound C | [structure] | IUPAC Name: 3-[(1S)-1-(1H-imidazol-4-yl)ethyl]-2-methylbenzyl 2-methylpropanoate |
| Compound D | [structure] | IUPAC Name: 3-[(1S)-1-(1H-imidazol-4-yl)ethyl]-2-methylbenzyl pivalate |
| Compound E | [structure] | IUPAC Name: 4-bromo-N-imidazolidin-2-ylidene-1H-benzimidazol-5-amine |
| Compound F | [structure] | IUPAC Name: (S)-(+)-7-(1H-Imidazol-4-ylmethyl)-5,6,7,8-tetrahydro-quinoline |
| Compound G | [structure] | IUPAC Name: 2-hydroxyethyl 5-(3-{(2S)-1-[4-(1-hydroxyhexyl)phenyl]-5-oxopyrrolidin-2-yl}propyl)thiophene-2-carboxylate |

TABLE 8-continued

Examples of APIs that may be formulated using PCA-PVA-PEG

| Drug class | Examples | Typical concentration range in Ophthalmic products |
|---|---|---|
| Compound H | | Cyclosporine Analog |

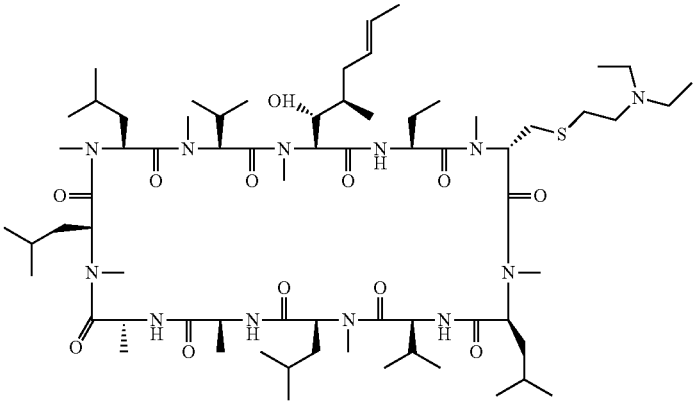 [SMILES: C/C=C/C[C@@H](C)[C@@H](O)[C@@H]1C(=O)N[C@H](CC)C(=O)N(C)[C@H](CSCCN(CC)CC)C(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N1C]

TABLE 9

Examples of Solution Formulations using PCA-PVA-PEG

| Ingredient type | Ingredient | Examples of typical conc. range % (w/w) |
|---|---|---|
| Active Ingredients | Any one or more of the drug substances listed in Table 8 | Any concentration of drug substances in ranges listed in Table 8 |
| Solubilizer/Preservative/Co-preservative | PCA-PVA-PEG | 0.001-5% |
| Secondary solubilizer/Co-solubilizer (may or may not be required) | SPAN™ 60 | 0-1% |
| | Pluronic F68 | 0-5% |
| | POE40Stearate | 0-1% |
| | CREMOPHOR EL ® | 0-1% |
| | Cyclodextrins | 0-10% |
| Osmolality agents (any one or two or more in | Propylene glycol | 0-2% |
| | Glycerin | 0-2.5% |
| | Mannitol | 0-5% |
| combinations) | Sodium chloride | 0-1% |
| Buffers (Any one of the buffers listed) | Phosphate buffer | 1-100 mM |
| | Phosphate citrate buffer | 1-100 mM |
| | NaOH/Trolamine | 1-100 mM |
| | Lactate buffer | 1-100 mM |
| | Borate buffer | 1-100 mM |
| | Borate citrate | 1-100 mM |
| | NaOH or HCl for pH adjustment | Q.S |
| Preservatives (Any one or in combination) | None - Non preserved | NA |
| | BAK | 10-200 ppm |
| | Purite | 10-300 ppm |
| | Water | QS |

TABLE 10

Examples of formulations containing PCA-PVA-PEG with non-aqueous components

| | Ointment Examples | Cream Examples % (w/w) | Microemulsion |
|---|---|---|---|
| Active Ingredients | | | |
| Any one or more of the drug substances listed in Table 8 | Any concentration of drug substances in ranges listed in Table 8 | | |
| Excipients | | | |
| SOLUPLUS ® | 0.1-5 | 0.1-3 | 0.1-3 | 0.67 |
| Water | QSAD | QSAD | QSAD | qs 100% |
| Propylene glycol | 10-15 | 5-20 | — | 2 |
| Glycerin | — | — | 8-12 | |
| Benzyl alcohol (preservative) | 1-5 | — | — | |
| Isopropyl myristate | — | 10-25 | — | |
| Carbopol 980 | — | 0.1-2% | 0.1-2 | |
| NaOH/Trolamine | — | QS pH 5.5-6.0 | QS pH 5.5-6.0 | |
| SPAN™ 60 | 1-5 | — | — | |
| Petrolatum | 20-30 | — | — | |
| Stearyl alcohol | 10-30 | — | 1-3 | |
| Pluronic F68 | — | 0.1-2 | — | |
| Stearic Acid | — | — | 10-15 | |

TABLE 10-continued

Examples of formulations containing PCA-PVA-PEG with non-aqueous components

| Cetyl Alcohol | — | — | 1-3 |
| Methyl/Propylparabens | — | — | PP 0.05 MP 0.1 |
| Capmul | | | 0.67 |
| CREMOPHOR EL ® | | | 0.67 |

| | Lipid Nanoparticle | Emulsion |
|---|---|---|
| | % (w/w) | |
| Ingredients | | |
| Active Ingredients Any one or more of the drug substances listed in Table 8 | Any concentration of drug substances in ranges listed in Table 8 | |
| Excipients | | |
| Medium chain triglyceride | 10-40 | — |
| Oleic acid | 0-0.5% | — |
| Water | QS | — |
| Castor Oil | — | 1.25 |
| SOLUPLUS ® | 0.01-5 | 0.01-2 |
| Glycerin | — | 2 |
| Carbopol 980 | 0.1-1% | 0.1-1 |
| Trolamine | Qs ad | Qs ad |

Examples of formulation vehicle compositions with Soluplus® in Tables 11-17. All of the formulations disclosed in Tables 11-17 may include an active agent from Table 8.

TABLE 11

Soluplus ® containing formulation vehicles with Boric acid buffer (Preservative-free)

| Ingredients | Range | Concentration (% w/v) Examples |||||||||
|---|---|---|---|---|---|---|---|---|---|---|
| Soluplus ® (Polyvinyl caprolactame - polyvinyl acetate- polyethylene glycol graft copolymer) | 0.1-10 | 10.0 | 2.0 | 1.0 | 1.0 | 0.75 | 0.5 | 0.25 | 0.1 | |
| Boric Acid | 0.1-1 | 0.6 | 0.6 | 0.6 | 0.6 | 0.6 | 0.6 | 0.6 | 0.6 | |
| Glycerin | | 1.2 | 1.2 | 1.2 | 1.2 | 1.2 | 1.2 | 1.2 | 1.2 | |
| 1N NaOH/1N HCl Qs to pH | 5.0-8.2 | 7.4 | 7.4 | 7.4 | 7.4 | 7.4 | 7.4 | 7.4 | 7.4 | |
| Water | QS | QS | QS | QS | QS | QS | QS | QS | QS | |

TABLE 12

Soluplus ® containing formulation vehicles with Boric acid buffer and Purite ® as preservative

| Ingredients | Range | Concentration (% w/v) Examples |||||||||
|---|---|---|---|---|---|---|---|---|---|---|
| Soluplus ® (Polyvinyl caprolactame - polyvinyl acetate- polyethylene glycol graft copolymer) | 0.1-10 | 10.0 | 2.0 | 1.0 | 1.0 | 0.75 | 0.5 | 0.25 | 0.1 | |
| Boric Acid | 0.1-1 | 0.6 | 0.6 | 0.6 | 0.6 | 0.6 | 0.6 | 0.6 | 0.6 | |
| Glycerin | | 1.2 | 1.2 | 1.2 | 1.2 | 1.2 | 1.2 | 1.2 | 1.2 | |
| Purite ® | 0.002-0.02 | 50 | 50 | 100 | 100 | 100 | 100 | 100 | 100 | |
| 1N NaOH/1N HCl Qs to pH | pH 5.0-8.2 | 7.4 | 7.4 | 7.4 | 7.4 | 7.4 | 7.4 | 7.4 | 7.4 | |
| Water | QS | QS | QS | QS | QS | QS | QS | QS | QS | |

TABLE 13

Soluplus ® containing formulation vehicles with citrate-phosphate buffer (preservative - free)

| Ingredients | Range | Concentration (% w/v) Examples | | | | | | | |
|---|---|---|---|---|---|---|---|---|---|
| Soluplus ® (Polyvinyl caprolactame - polyvinyl acetate- polyethylene glycol graft copolymer) | 0.1-10 | 1.0 | 1.0 | 1.0 | 2.0 | 2.0 | 5.0 | 0.5 | 0.5 |
| Sodium Phosphate Dibasic Heptahydrate | 0.03-3 | 0.268 | 0.268 | 0.268 | 0.268 | 0.268 | 0.268 | 0.268 | 0.268 |
| Citric Acid Monohydrate | 0.001-0.15 | 0.014 | 0.014 | 0.014 | 0.014 | 0.014 | 0.014 | 0.014 | 0.014 |
| Glycerin | 0-3 | 1.2 | 1.2 | 1.2 | 1.2 | 1.2 | 1.2 | 1.2 | 1.2 |
| Mannitol | 0-5 | 2.0 | 2.0 | 2.0 | 2.0 | 2.0 | 2.0 | 2.0 | 2.0 |
| 1N NaOH/1N HCl Qs to pH | 5.0-8.2 | 7.3 | 7.4 | 7.4 | 7.4 | 7.4 | 7.4 | 7.4 | 7.4 |
| Water | | QS | QS | QS | QS | QS | QS | QS | QS |

TABLE 14

Soluplus ® containing formulation vehicles with citrate-phosphate buffer and Benzalkonium chloride (BAK) as preservative

| Ingredients | Range | Concentration (% w/v) Examples | | | | | | | |
|---|---|---|---|---|---|---|---|---|---|
| Soluplus ® (Polyvinyl caprolactame - polyvinyl acetate- polyethylene glycol graft copolymer) | 0.1-10 | 1.0 | 1.0 | 1.0 | 2.0 | 2.0 | 5.0 | 0.5 | 0.5 |
| Benzalkonium Chloride | 0.003-0.02 | 0.005 | 0.010 | 0.020 | 0.012 | 0.014 | 0.016 | 0.01 | 0.020 |
| Sodium Phosphate Dibasic Heptahydrate | 0.03-3 | 0.268 | 0.268 | 0.268 | 0.268 | 0.268 | 0.268 | 0.268 | 0.268 |
| Citric Acid Monohydrate | 0.001-0.15 | 0.014 | 0.014 | 0.014 | 0.014 | 0.014 | 0.014 | 0.014 | 0.014 |
| Glycerin | 0-3 | 1.2 | 1.2 | 1.2 | 1.2 | 1.2 | 1.2 | 1.2 | 1.2 |
| Mannitol | 0-5 | 2.0 | 2.0 | 2.0 | 2.0 | 2.0 | 2.0 | 2.0 | 2.0 |
| 1N NaOH/1N HCl Qs to pH | 5.0-8.2 | 7.3 | 7.4 | 7.4 | 7.4 | 7.4 | 7.4 | 7.4 | 7.4 |
| Water | | QS | QS | QS | QS | QS | QS | QS | QS |

TABLE 15

Soluplus ® containing formulation vehicles with citrate-phosphate buffer, Benzalkonium chloride (BAK) as preservative and EDTA

| Ingredients | Range | Concentration (% w/v) Examples | | | | | | | |
|---|---|---|---|---|---|---|---|---|---|
| Soluplus ® (Polyvinyl caprolactame - polyvinyl acetate- polyethylene glycol graft copolymer) | 0.1-10 | 1.0 | 1.0 | 1.0 | 2.0 | 2.0 | 5.0 | 0.5 | 0.5 |
| Benzalkonium Chloride | 0.003-0.02 | 0.005 | 0.010 | 0.020 | 0.012 | 0.014 | 0.016 | 0.01 | 0.020 |
| Edetate Disodium | 0-0.05 | 0.01 | 0.01 | 0.01 | 0.01 | 0.01 | 0.01 | 0.005 | 0.005 |
| Sodium Phosphate Dibasic Heptahydrate | 0.03-3 | 0.268 | 0.268 | 0.268 | 0.268 | 0.268 | 0.268 | 0.268 | 0.268 |
| Citric Acid Monohydrate | 0.001-0.15 | 0.014 | 0.014 | 0.014 | 0.014 | 0.014 | 0.014 | 0.014 | 0.014 |
| Glycerin | 0-3 | 1.2 | 1.2 | 1.2 | 1.2 | 1.2 | 1.2 | 1.2 | 1.2 |
| Mannitol | 0-5 | 2.0 | 2.0 | 2.0 | 2.0 | 2.0 | 2.0 | 2.0 | 2.0 |
| 1N NaOH/1N HCl Qs to pH | 5.0-8.2 | 7.3 | 7.4 | 7.4 | 7.4 | 7.4 | 7.4 | 7.4 | 7.4 |
| Water | | QS | QS | QS | QS | QS | QS | QS | QS |

TABLE 16

Examples of Emulsion Vehicles with Soluplus (Preservative-Free)

| Ingredients | Range | Concentration (% w/v or % w/w) Examples | | | | | | | | | |
|---|---|---|---|---|---|---|---|---|---|---|---|
| Castor Oil | 0.1-10 | 0.25 | 0.5 | 1.25 | 1.25 | 0.25 | 0.5 | 1.25 | 0.25 | 0.5 | 1.25 |
| Polysorbate 80 | 0-2 | 0 | 0 | 0 | 0 | 0.25 | 0.5 | 0.5 | 0 | 0 | 0 |
| Solutol ® | 0-5 | 0 | 0.5 | 0.5 | 1 | 0.25 | 0.5 | 0.5 | 0 | 0 | 0 |
| Polyoxyethylene 40 Stearate | 0-5 | 0.25 | 0.5 | 0.5 | 1 | 0 | 0 | 0 | 0.5 | 1 | 2 |
| Soluplus ® (Polyvinyl caprolactame - polyvinyl acetate- polyethylene glycol graft copolymer) | 0.01-2 | 0.25 | 0.5 | 2 | 2 | 0.5 | 0.5 | 1.0 | 1 | 2 | 2 |
| Glycerin | 0.5-3 | 2.5 | 2.5 | 2.5 | 2.5 | 2.5 | 2.5 | 2.5 | 2.5 | 2.5 | 2.5 |
| Carbopol 980 | 0.1-1 | 0.1 | 0.1 | 0.1 | 0.1 | 0.1 | 0.1 | 0.1 | 0.1 | 0.1 | 0.1 |
| Trolamine or NaOH | QS | QS to pH 6 to 8 | | | | | | | | | |
| Water QS to 100% | QS | QS | QS | QS | QS | QS | QS | QS | QS | QS | QS |

TABLE 17

Examples of Emulsion Vehicles with Soluplus (Preserved with Purite, Benzalkonium chloride or combination). Any of the vehicles in Table 6 with the following ingredients as preservatives

| Ingredients | Range | Concentration Examples | | | | | | | | | |
|---|---|---|---|---|---|---|---|---|---|---|---|
| Purite | 50-200 ppm | 50 | 100 | 200 | 50 | 50 | 100 | 100 | 0 | 0 | 0 |
| Benzalkonium chloride | 10-200 ppm | 0 | 0 | 0 | 20 | 50 | 20 | 200 | 50 | 100 | 200 |
| Any of the vehicles from Table 6 | | QS to 100% w/v or % w/w | | | | | | | | | |

Example 8

Some topical ophthalmic compositions comprise a polyvinyl caprolactam-polyvinyl acetate-polyethylene glycol graft copolymer.

Example 9

In some compositions of Example 8, the polyvinyl caprolactam-polyvinyl acetate-polyethylene glycol graft copolymer has an average molecular weight of about 10,000 g/mol to about 500,000 g/mol.

Example 10

Some compositions of Example 8 or 9 further comprise a therapeutically active agent.

Example 11

In some compositions of Example 10, the therapeutically active agent comprises an immunosuppressant.

Example 12

In some compositions of Example 10, the therapeutically active agent comprises an alpha-adrenergic antagonist.

Example 13

In some compositions of Example 10, the therapeutically active agent comprises a prostaglandin EP2 agonist.

Example 14

In some compositions of Example 10, the therapeutically active agent comprises a muscarinic.

Example 15

In some compositions of Example 10, the therapeutically active agent comprises a prostaglandin.

Example 16

In some compositions of Example 10, the therapeutically active agent comprises an alpha agonist.

Example 17

In some compositions of Example 10, the therapeutically active agent comprises an antibiotic.

Example 18

In some compositions of Example 10, the therapeutically active agent comprises an anti-infective agent.

Example 19

In some compositions of Example 10, the therapeutically active agent comprises an anti-inflammatory.

Example 20

In some compositions of Example 10, the therapeutically active agent comprises a beta blocker.

Example 21

In some compositions of Example 10, the therapeutically active agent comprises cyclosporine A.

Example 22

In some compositions of Example 10, the therapeutically active agent comprises a cyclosporine analog.

Example 23

In some compositions of Example 10, the therapeutically active agent comprises phentolamine.

Example 24

In some compositions of Example 10, the therapeutically active agent comprises testosterone.

Example 25

In some compositions of Example 10, the therapeutically active agent comprises dexamethasone.

Example 26

In some compositions of Example 10, the therapeutically active agent comprises prednisolone.

Example 27

In some compositions of Example 10, the therapeutically active agent comprises bimatoprost.

Example 28

In some compositions of Example 10, the therapeutically active agent comprises latanoprost.

Example 29

In some compositions of Example 10, the therapeutically active agent comprises Compounds A or B of Table 8.

Example 30

In some compositions of Example 10, the therapeutically active agent comprises pilocarpine.

Example 31

In some compositions of Example 10, the therapeutically active agent comprises brimonidine.

Example 32

In some compositions of Example 10, the therapeutically active agent comprises Compound C of Table 8.

Example 33

In some compositions of Example 10, the therapeutically active agent comprises Compound D of Table 8.

Example 34

In some compositions of Example 10, the therapeutically active agent comprises Compound E of Table 8.

Example 35

In some compositions of Example 10, the therapeutically active agent comprises Compound F or G of Table 8.

Example 36

In some compositions of Example 10, the therapeutically active agent comprises gatifloxacin.

Example 37

In some compositions of Example 10, the therapeutically active agent comprises ketorolac.

Example 38

In some compositions of Example 10, the therapeutically active agent comprises a steroid.

Example 39

In some compositions of Example 10, the therapeutically active agent comprises timolol.

Example 40

In some compositions of Example 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39, the composition is a solution.

Example 41

Some compositions of Example 40 further comprise a co-solubilizer.

Example 42

In some compositions of Example 41, the co-solubilizer comprises sorbitan monostearate.

Example 43

In some compositions of Example 41, the co-solubilizer comprises a polyoxyethylene-polyoxypropylene block copolymer.

Example 44

In some compositions of Example 41, the co-solubilizer comprises polyoxyethyleneglyceroltriricinoleate 35.

Example 45

In some compositions of Example 41, the co-solubilizer comprises a cyclodextrin.

Example 46

Some compositions of Example 40, 41, 42, 43, 44, or 45 further comprise an osmolality agent.

Example 47

In some compositions of Example 46, the osmolality agent comprises propylene glycol.

Example 48

In some compositions of Example 46, the osmolality agent comprises glycerin.

Example 49

In some compositions of Example 46, the osmolality agent comprises mannitol.

Example 50

In some compositions of Example 46, the osmolality agent comprises sodium chloride.

Example 51

Some compositions of Example, 40, 41, 42, 43, 44, 45, 46, 47, 48, 49, or 50 further comprise a buffer.

Example 52

In some compositions of Example 51, the buffer comprises phosphate.

Example 53

In some compositions of Example 51, the buffer comprises phosphate and citrate.

Example 54

In some compositions of Example 51, the buffer comprises trolamine.

Example 55

In some compositions of Example 51, the buffer comprises lactate.

Example 56

In some compositions of Example 51, the buffer comprises borate.

Example 57

In some compositions of Example 51, the buffer comprises borate and citrate.

Example 58

Some compositions of Example, 40, 41, 42, 43, 44, 45, 46, 47, 48, 49, 50, 51, 52, 53, 54, 55, 56, or 57 further comprise a preservative.

Example 59

In some compositions of Example 58, the preservative comprises benzalkonium chloride.

Example 60

In some compositions of Example 58, the preservative comprises a stabilized oxychloro complex.

Example 61

A method of solubilizing a therapeutically active agent comprising mixing the therapeutically active agent and a polyvinyl caprolactam-polyvinyl acetate-polyethylene glycol graft copolymer so that a composition according to any of Examples 10-60 is formed.

Example 62

A method of stabilizing a therapeutically active agent comprising combining the therapeutically active agent with a polyvinyl caprolactam-polyvinyl acetate-polyethylene glycol graft copolymer to thereby improve stability of the therapeutically active agent.

Example 63

A method of stabilizing a therapeutically active agent comprising combining the therapeutically active agent and a polyvinyl caprolactam-polyvinyl acetate-polyethylene glycol graft copolymer so that a composition according to any of Examples 10-60 is formed.

Example 64

A method of treating a disease affecting an eye comprising administering a composition according to any Examples 8-60 to an eye in need thereof.

Example 65

A 65 year old Caucasian male suffering from elevated intraocular pressure applies one drop per day of Formula 2 of Table 18 in each eye for a period of 60 days. The patient experiences a significant drop in IOP almost immediately which persists for the entire 60 days of treatment wherein his intraocular pressure levels drop to acceptable levels.

TABLE 18

|  | Formulation # | | |
| --- | --- | --- | --- |
|  | 1 | 2 | 8 |
| Ingredient (% w/v) | | | |
| Bimatoprost | 0.01 | 0.01 | 0.01 |
| Brimonidine (190342-LF) | 0.1 | 0.1 | 0.1 |
| Soluplus | 1 | 1 | 1 |
| Sodium phosphate dibasic heptahydrate | 0.268 |  | 0.268 |
| Citric acid monohydrate | 0.014 |  | 0.014 |
| Sodium borate decahydrate |  | 0.095 |  |
| Boric acid |  | 0.229 |  |
| NaCl |  |  | 0.8 |
| Glycerin | 2.3 | 2.3 |  |
| BAK | 0.005 |  | 0.01 |
| Purite |  | 0.01 |  |

TABLE 18-continued

| | Formulation # | | |
|---|---|---|---|
| | 1 | 2 | 8 |
| Target pH | pH 7.7 ± 0.3 | | |
| Purified Water | Q.S. to 100 | | |
| APET Criteria Met | | | |
| USP | Pass | Pass | Pass |
| Ph Eur B | Pass | Pass | Pass |
| Ph Eur A | Pass | Fail | Pass |

Example 66

A 71 year old African American woman suffering from elevated intraocular pressure and open-angle glaucoma applies one drop daily in each eye of Formula 4 from Table 19. After 30 days, her symptoms of glaucoma improve significantly and her intraocular pressure falls to normal levels and without significant side effects so long as she continued daily application of Formula 4 of Table 19.

TABLE 19

| | Active Formulation # | | | | | |
|---|---|---|---|---|---|---|
| Ingredient (% w/v) | 1 | 2 | 3 | 4 | 5 | 6 |
| Compound D Of Table 8 | 0.4 | 0.4 | 0.4 | 0.4 | 0.4 | 0.4 |
| Soluplus | 1 | 1 | 1 | 1 | 1 | 2 |
| BAK | 0 | 0.005 | 0.010 | 0.015 | 0.020 | 0.020 |
| Edetate Disodium | 0.01 | 0.01 | 0.01 | 0.01 | 0.01 | 0.01 |
| Citric Acid Monohydrate | 0.13 | 0.13 | 0.13 | 0.13 | 0.13 | 0.13 |
| Sodium Phosphate Dibasic Heptahydrate | 0.2 | 0.2 | 0.2 | 0.2 | 0.2 | 0.2 |
| Glycerin | 2.2 | 2.2 | 2.2 | 2.2 | 2.2 | 2.2 |
| Target pH | pH 5.4 | | | | | |
| Purified Water | Q.S. to 100 | | | | | |
| APET Criteria Met | | | | | | |
| USP | Pass | Pass | Pass | Pass | Pass | Pass |
| Ph Eur B | Pass | Pass | Pass | Pass | Pass | Pass |
| Ph Eur A | Fail | Fail | Fail | Fail | Pass | Pass |

A 41 year old Caucasian female is suffering from symptoms of dry eye, applies twice daily Formulation 2 in Table 20 in each eye. After two days of application, the symptoms of dry eye improve significantly.

TABLE 20

| | Formulation # | |
|---|---|---|
| | 1 | 2 |
| Ingredient (% w/v) | | |
| Soluplus | 2 | 5 |
| Boric Acid | 0.6 | 0.6 |
| Glycerin | 2 | 2 |
| Target pH | pH 7.4 | |
| Purified Water | Q.S. to 100 | |
| APET Criteria Met | | |
| USP | Pass | Pass |
| Ph Eur B | Pass | Pass |
| Ph Eur A | Fail | Fail |

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A method of increasing the preservative efficacy of a benzalkonium chloride-containing aqueous solution, wherein the method comprises providing a first composition comprising benzalkonium chloride in combination with a polyvinyl caprolactam-polyvinyl acetate-polyethylene glycol graft copolymer; wherein the preservative efficacy of the first composition is increased in comparison to a second composition containing benzalkonium chloride but not containing polyvinyl caprolactam-polyvinyl acetate-polyethylene glycol graft copolymer.

2. The method of claim 1, wherein the first composition contains benzalkonium chloride at a concentration of 160 ppm or below and meets Ph Eur-A criteria.

3. The method of claim 2, wherein the benzalkonium chloride is present at a concentration at or below 50 ppm.

4. The method of claim 2, wherein the benzalkonium chloride is present at a concentration at or below 100 ppm.

5. The method of claim 1, wherein the first composition contains a polyvinyl caprolactam-polyvinyl acetate-polyethylene glycol graft copolymer at a concentration at or below 1% and meets Ph Eur-A criteria.

6. The method of claim 1, wherein the aqueous solution is an ophthalmic solution.

7. The method of claim 1, wherein the polyvinyl caprolactam-polyvinyl acetate-polyethylene glycol graft copolymer has an average molecular weight of about 10,000 g/mol to about 500,000 g/mol.

8. The method of claim 1, wherein the first composition further comprises at least one therapeutically active agent.

9. The method of claim 8, wherein the therapeutically active agent comprises an immunosuppressant, an alpha-adrenergic antagonist, a steroid, a prostaglandin EP2 agonist, a muscarinic, a prostaglandin, an alpha agonist, an antibiotic, an anti-infective agent, an anti-inflammatory, a beta blocker, or a combination thereof.

10. The method of claim 1, wherein the first composition further comprises one or more osmolality agents.

11. The method of claim 10, wherein the one or more osmolality agents are selected from the group consisting of propylene glycol, glycerin, mannitol, sodium chloride, or a combination thereof.

12. The method of claim 1, wherein the first composition further comprises one or more buffering agents.

13. The method of claim 12, wherein the one or more buffering agents are selected from the group consisting of phosphate, phosphate and citrate, trolamine, lactate, borate, borate and citrate, or a combination thereof.

14. The method of claim 1, wherein the first composition further comprises a stabilized oxychloro complex.

15. A method of increasing the preservative efficacy of a stabilized oxychloro complex-containing aqueous solution, wherein the method comprises providing a composition comprising stabilized oxychloro complex in combination with a polyvinyl caprolactam-polyvinyl acetate-polyethylene glycol graft copolymer.

16. The method of claim 15, wherein the stabilized oxychloro complex is present at a concentration at or below 0.01% w/v.

17. The method of claim 16, wherein the stabilized oxychloro complex is present at a concentration from 0.002% to 0.01% w/v.

18. The method of claim 15, wherein the polyvinyl caprolactam-polyvinyl acetate-polyethylene glycol graft copolymer is present at a concentration from 0.1% to 1% w/v.

19. The method of claim 15, wherein the polyvinyl caprolactam-polyvinyl acetate-polyethylene glycol graft copolymer has an average molecular weight of about 10,000 g/mol to about 500,000 g/mol.

20. The method of claim 15, wherein the composition meets Ph Eur-A criteria.

21. The method of claim 15, wherein the composition meets Ph Eur-B criteria.

22. The method of claim 15, wherein the composition further comprises boric acid.

23. The method of claim 15, wherein the first composition further comprises at least one therapeutically active agent.

24. The method of claim 23, wherein the therapeutically active agent comprises an immunosuppressant, an alpha-adrenergic antagonist, a steroid, a prostaglandin EP2 agonist, a muscarinic, a prostaglandin, an alpha agonist, an antibiotic, an anti-infective agent, an anti-inflammatory, a beta blocker, or a combination thereof.

25. The method of claim 15, wherein the first composition further comprises one or more osmolality agents.

26. The method of claim 25, wherein the one or more osmolality agents are selected from the group consisting of propylene glycol, glycerin, mannitol, sodium chloride, or a combination thereof.

27. The method of claim 15, wherein the first composition further comprises one or more buffering agents.

28. The method of claim 27, wherein the one or more buffering agents are selected from the group consisting of phosphate, phosphate and citrate, trolamine, lactate, borate, borate and citrate, or a combination thereof.

29. A method of increasing the preservative efficacy of a solution containing a preservative, wherein the method comprises providing a solution comprising a polyvinyl caprolactam-polyvinyl acetate-polyethylene glycol graft copolymer in combination with the preservative.

30. The method of claim 29, wherein the preservative is selected from the group consisting of benzalkonium chloride, stabilized oxychloro complex, or a combination thereof.

31. The method of claim 30, wherein the preservative is benzalkonium chloride.

32. The method of claim 31, wherein the benzalkonium chloride is present at a concentration from 50 to 160 ppm.

33. The method of claim 30, wherein the preservative is stabilized oxychloro complex.

34. The method of claim 33, wherein the stabilized oxychloro complex is present at a concentration from 0.002% to 0.01% w/v.

35. The method of claim 29, wherein the polyvinyl caprolactam-polyvinyl acetate-polyethylene glycol graft copolymer has an average molecular weight of about 10,000 g/mol to about 500,000 g/mol.

36. The method of claim 29, wherein the first composition further comprises at least one therapeutically active agent.

37. The method of claim 36, wherein the therapeutically active agent comprises an immunosuppressant, an alpha-adrenergic antagonist, a steroid, a prostaglandin EP2 agonist, a muscarinic, a prostaglandin, an alpha agonist, an antibiotic, an anti-infective agent, an anti-inflammatory, a beta blocker, or a combination thereof.

* * * * *